US006465207B1

(12) United States Patent
Leek

(10) Patent No.: US 6,465,207 B1
(45) Date of Patent: Oct. 15, 2002

(54) SILVER-BASED STAINING PROCESSES EMPLOYING NON-GELLING GELATIN

(75) Inventor: Adrian Elmer Leek, Hingham, MA (US)

(73) Assignee: CytoLogix Corporation, Cambridge, MA (US)

( * ) Notice: Subject to any disclaimer, the term of this patent is extended or adjusted under 35 U.S.C. 154(b) by 3 days.

(21) Appl. No.: 09/706,537

(22) Filed: Nov. 3, 2000

(51) Int. Cl.$^7$ .............................. C12Q 1/04; C12Q 1/00; G01N 1/30; C12P 39/00
(52) U.S. Cl. .......................... 435/34; 435/40.5; 435/42; 435/4
(58) Field of Search ........................... 435/34, 40.5, 42, 435/4

(56) References Cited

U.S. PATENT DOCUMENTS

| | | | | |
|---|---|---|---|---|
| 4,147,772 A | * | 4/1979 | McAleer et al. | 424/212.1 |
| 4,273,762 A | | 6/1981 | McAleer et al. | 424/89 |
| 4,338,335 A | | 7/1982 | McAleer et al. | 424/361 |
| 5,316,452 A | | 5/1994 | Bogen et al. | 417/412 |
| 5,645,114 A | | 7/1997 | Bogen et al. | 141/145 |
| 5,695,942 A | | 12/1997 | Farmilo et al. | 485/7.1 |
| 5,965,454 A | | 10/1999 | Farmilo et al. | 436/180 |
| 6,086,893 A | * | 7/2000 | Dupuy et al. | 435/7.32 |
| 6,092,659 A | | 7/2000 | Loeffler et al. | 222/207 |

OTHER PUBLICATIONS

Rhatigan–Drexler, K., "A Comparison of Staining Methods for *Helicobacter pylori*," *Histo–Logic*, 30: 3–8 (1999), published by Sakura Finetek Inc., Torrance, CA.

Luna, L.G., "Methods for Bacteria, Fungi, and Inclusion Bodies," *Manual of Histologic Staining Methods of the Armed Forces Institute of Pathology 3$^{rd}$ Ed.*, Editor, L.G. Luna, 238–240 (1968).

Luna, L.G., "Methods for Staining *Helicobacter pylori*," *Histopathologic Methods and Color Atlas of Special Stains and Tissue Artifacts*, 216–218 (1992).

Luna, L.G., "Modified Steiner Technique for Spirochetes and *Helicobacter pylori*," *Histopathologic Methods and Color Atlas of Special Stains and Tissue Artifacts*, 218–219 (1992).

Brochure from DynaGel, Inc. re: Sol–U–Pro.
Brochure from DynaGel, Inc. re: Gelatin.

Stevens, A. and Francis, R.J., "Micro–organisms," Theory and Practice of Historical Techniques, Editors: Bancroft, J.D. and Stevens, A.,4$^{th}$ Edition Churchill Livingstone (1976).

Tokunaga, Y., et al. "Proliferation Potentials of Human Intracranial Neoplasms Assessed with Ki–67(MIB–1) Labeling Index and Argyrophilic Nucleolar Organizer Regions", Acta Medica Nagasakiensia 42:44–50 (1997).

* cited by examiner

*Primary Examiner*—Louise N. Leary
(74) *Attorney, Agent, or Firm*—Hamilton, Brook, Smith and Reynolds, P.C.

(57) ABSTRACT

An automated method for the silver metal staining of a biological specimen includes treating the biological specimen with a solution including non-gelling gelatin, a solution including a silver salt and a solution including a reducing agent. Non-gelling gelatin is soluble in cold water and the non-gelling gelatin solution can be formed and dispensed onto the biological specimen from liquid dispensers at room temperature. The method can be used in an automated process to detect spirochetes and other bacteria in tissue sections.

21 Claims, No Drawings

SILVER-BASED STAINING PROCESSES EMPLOYING NON-GELLING GELATIN

BACKGROUND OF THE INVENTION

The presence of microorganisms, such as spirochetes or bacteria, for instance Helicobacter pylori, in tissue samples can be detected by histological stains such as the Warthin-Starry silver stain. The stain generally involves combining a silver nitrate solution with gelatin and hydroquinone. Since gelatin is typically a solid at room temperature, the manual stain protocol generally includes liquifying the gelatin, typically by warming it, such as in a microwave oven, prior to its use in the staining process. Generally temperatures as high as 56° C. are used.

One existing automated histo-cytochemistry slide staining system dispenses a solid gelatin matrix. Upon heating, the gelatin matrix forms a solution. In a number of automated staining systems, however, it is preferred to dispense staining reagents that are liquid at room temperature. Such systems cannot currently employ the Warthin Starry staining approach because of the high temperature required to liquify gelatin. As a result, alternative protocols which do not require gelatin but which often are complex and time consuming are currently being used.

Therefore a need exists for simplified automated staining procedures based on the selective deposition of silver metal which can employ liquid dispensers to dispense room temperature staining reagents.

SUMMARY OF THE INVENTION

The methods of the present invention are directed to staining processes whose protocols include the use of gelatin. One specific example of such a staining process is the Warthin Starry method generally used to detect the presence of microorganisms, such as spirochetes, or other bacteria in a biological specimen. The methods described herein are particularly suited for performing automated staining processes using delivery of liquid reagents at room temperature and preferably from liquid dispensers. The methods described herein also provide advantages for staining procedures that are performed manually.

The methods of the invention include replacing gelatin, which generally requires heating to liquify or dissolve in water with non-gelling gelatin, a partially hydrolyzed gelatin. Non-gelling gelatin is soluble in water at room temperature, i.e., about 19° Celsius (C) to about 25° C. Furthermore, aqueous solutions of non-gelling gelatin in water are not viscous at concentrations such as those employed in the staining procedures described herein.

In a preferred embodiment of the invention, a biological specimen is stained by the selective deposition of silver metal. The staining method includes treating the biological specimen with an aqueous solution of non-gelling gelatin, a solution including a silver salt, e.g., silver nitrate, and a solution including a reducing agent, e.g., hydroquinone. The reaction of the reducing agent with the silver salt results in the formation of silver metal which is selectively deposited in some spirochetes, microorganisms or tissue abnormalities and visualizes their presence in the biological specimen.

The invention has many advantages. For example, it can be used to simplify existing manual staining protocols. It also allows the use of existing automated slide staining systems which employ liquid dispensers and room temperature dispensing to carry out staining procedures which could not be previously automated for such systems.

DETAILED DESCRIPTION OF THE INVENTION

The invention is related to staining procedures of biological specimens.

Examples of biological specimens include, but are not limited to, tissue sections, cell cultures, nasal, vaginal, urethral smears, control samples and cytospins. In one embodiment of the invention, the biological specimen is a tissue sample, for instance a tissue sample suitable for histological staining. The biological specimen is prepared as known in the art. In one embodiment of the invention, the biological specimen is a paraffin embedded tissue section after fixation with 10% neutral buffered formalin or other fixative.

Numerous staining procedures, also referred to herein as staining protocols, staining processes, staining methods, stains or staining, have been developed to visualize cell or tissue abnormalities and to detect, identify or characterize microorganisms present in a biological specimen. During histological, cytological or histopathological staining protocols a biological specimen is contacted with staining reagents, also referred to herein as staining solutions or solutions. The sequence and amounts in which the staining reagents are added to the biological specimen depend on the particular staining procedure, as known in the art. Special stains generally include numerous steps and often are some of the most complex tests performed in the laboratory. A number of special stains have been developed for the histological analysis of tissue samples. For example, special stains exists for determining the presence of microorganisms, such as would occur in the context of pathogen invasion, colonization or contamination of a biological specimen, for instance a tissue sample. Such stains are referred to herein as histologic stains.

The invention is generally related to staining procedures which employ gelatin. In one embodiment of the invention, the staining procedure includes the selective deposition, also referred to herein as selective impregnation, with silver. In another embodiment of the invention, the staining procedure is related to detecting a microorganism, a cell or tissue abnormality or a cell or tissue component which is argyrophilic. By argyrophilic it is meant herein that the microorganism, cell or tissue abnormality or component has the property of selectively absorbing silver from a silver salt solution. Generally, staining techniques which rely on the selective impregnation with silver show, against a lighter background not impregnated with silver, a metallic silver image, typically black, which indicates and helps visualize the presence of a pathogen, microorganism, cell or tissue component or abnormality.

Stain protocols which rely on visualizing silver metal that has been selectively deposited often require combining a silver salt solution with a gelatin solution. Aqueous solutions are preferred. One suitable silver salt is silver nitrate. Other silver salts that can be employed in such procedures include but are not limited to silver acetate, silver chlorate and silver fluoride.

Without wishing to be bound by any particular mechanism, it is believed that the role gelatin plays in these stains is somewhat similar to its role in black and white photography. For example, it is believed, that gelatin serves as a protective colloid and has good coating and adhesion properties when used in photographic processes. It is also believed that some of the chemical reactions taking place during stain processes which rely on the formation of metallic silver also parallel chemical reactions which occur in developing black and white photographs. For example, such stain protocols include the addition of a reducing agent, often hydroquinone, a phenolic compound widely employed in photographic processes. As silver is reduced to its metallic state, it is believed that hydroquinone is oxidized to quinone. Examples of other suitable reducing agents include, but are not limited to catechol and other o- and p-dihydroxy or hydroxyamine aromatic compounds.

In a preferred embodiment, the staining procedure is a procedure for detecting spirochetes or bacteria. One particular organism that can be detected using the methods of the invention is *Helicobacter pylori*, (*H. pylori*), a bacterium associated with active chronic gastritis and peptic ulcers. *Helicobacter pylori* is discussed, for example, by Rhatigan-Drexler, K., "A Comparison of Staining Methods for Helicobacter pylori," Histo-Logic, 30: 3–8 (1999), published by Sakura Finetek Inc., Torrance, Calif.

Examples of other specific microorganisms that can be detected by the methods of the invention include, but are not limited to, *Staphylococcus aureus, Neisseria meningitidis,* Neisseria Gonorrhoeae, Lactobacillus Acidophilus, Corynebacterium Vaginale, *Clostridium diffcile, Listeria monocytogenes*, and others.

The methods of the invention are suitable for other stains whose protocols call for using gelatin. For example, the invention can be used in conjunction with staining procedures for argyrophilic nucleolar organizer regions, commonly abbreviated as Ag-NORs.

A staining process particularly preferred herein is based on the Warthin Starry staining method which is frequently used to detect the presence of spirochetes. Protocols for the manual Warthin Starry stain are described, for example in Bridges, C. H. and Luna, L. G., "Methods for Bacteria, Fungi, and Inclusion Bodies," *Manual of Histologic Staining Methods of the Amed Forces Institute of Pathology* 3$^{rd}$ Edition, Editor, Lee G. Luma (1968); Luna, Lee, G., "Methods for Staining *Helicobacter Pylori,*" *Histopathologic Methods and Color Atlas of Special Stains and Tissue Artifacts*, 216–218 (1992).

The existing protocols for the Warthin Starry staining method generally involve a gelatin solution, for example, a 5% aqueous gelatin solution. A typical procedure for preparing the gelatin solution is to combine solid (sheet) gelatin and water at a temperature high enough to dissolve the solid gelatin. For example, the gelatin is combined with water heated to 56° C. for 15 minutes. One particular existing Warthin-Starry protocol, for example, calls for combining 10.0 grams of high grade sheet gelatin with 200.0 ml acidulated water to form a 5% gelatin solution. According to the same protocol, 1.5 ml of a 2% silver nitrate solution is combined with 3.75 ml of the 5% gelatin solution and 2.0 ml of 0.15% hydroquinone solution to form a developer solution. A tissue section to be stained is deparaffinized and hydrated after which it is impregnated with silver nitrate solution in a floatation bath at 43° C. The impregnated section is then flooded with the developer solution and the section is allowed to develop to a light brown or yellow color. The presence of spirochetes can be ascertained under a microscope, by comparison with a control. The spirochetes appear black against a light brown or yellow background.

The invention is particularly related to automated staining processes and can be employed in a number of automated staining protocols and in conjunction with instruments, controls and software known in the art. The skilled practitioner also can employ the present invention, without undue experimentation, in conjunction with new automated staining procedures, new instrumentation, control systems and software as such are being developed.

Examples of automated equipment for carrying out the invention include the Artisan™ Staining System provided by CytoLogix™ Corporation, Cambridge, Mass., and systems such as those provided by Ventana Medical Systems, Biogenex, Dako, Shandon, Leica and others.

During automated procedures the biological specimen is affixed, smeared, attached, supported or otherwise provided, generally on a planar platform, such as a microscope slide. More than one specimen can be provided on a single slide. Commonly, the slide is a glass slide but slides made out of other materials that are compatible with the biological specimen and staining reagents can also be used. Optionally, the slides can be separated from one another by dividing walls, thereby preventing reagent spills from one slide to another.

In a preferred configuration such as described for the Artisan™ slide staining system, discussed below, the slide is held on a rotating platform and staining reagents are dispensed from liquid dispensers held by a moving platform, for example a rotating carousel. As the liquid dispensers move into position over a desired slide, they dispense staining reagents in the amounts and in the sequence specified by the particular staining protocol. The protocols often include washing steps as well as steps for the collection of spent reagents and/or their disposal. Automated staining procedures generally are controlled by control systems integrated with computer software, as known in the art. Alternatively, slides supporting the biological specimens can move underneath a non-moving platform holding the liquid dispensers, or both platforms may rotate or otherwise move to bring a particular slide and a particular dispenser together for the dispensing operation.

The Artisan™ slide staining system, sold by CytoLogix Corporation, is a particularly preferred configuration for using this invention. A slide bearing a thin biologic specimen, such as a tissue section or cells, is positioned on a rotary carousel. The carousel's positioning is specified under computer control, according to a pre-set program specified by the operator of the instrument. A second rotary carousel for carrying reagents (in liquid dispensers) is located above the carousel for holding slides. The positioning of the second carousel is also under computer control. To dispense a desired reagent onto a specific microscope slide, the two carousels are rotated so that a dispenser holding a reagent (mounted on the upper carousel) is positioned above a desired slide. An actuator causes the dispenser to dispense reagent onto the slide. The amount and sequence of reagent applications to slides are specified by the particular staining protocol. The protocols often include washing steps, to remove reagent after the reaction has completed. The protocols also provide for the collection of spent reagent into selected containers. Automated staining procedures generally are controlled by control systems integrated with computer software, as known in the art.

Suitable liquid dispensers which can be employed in automated staining are described, for instance, in U.S. Pat. Nos. 5,645,114 and 5,316,452 to Steven A. Bogen, et al.; both are incorporated herein by reference in their entirety. A preferred liquid dispenser design is described in U.S. Pat. No. 6,092,695 to Herbert H. Loeffler, the entire contents of which are incorporated herein by reference.

The slide temperature in the automated systems discussed above is adjustable and thus the biological specimen and the staining reagents dispensed onto it can be warmed to and/or maintained at a specified temperature. However, it is preferred to dispense solutions of staining reagents at room temperature. Since at room temperature gelatin solutions are solid, they cannot be readily used in conjunction with room temperature liquid dispensing.

Alternative staining protocols, for similar microorganiams such as the Steiner procedure do not require gelatin. A manual, i.e., non-automated, protocol based on the Steiner method is presented, for example, in Luna, Lee, G., "Modified Steiner Technique for Spirochetes and Helicobacter Pylori," *Histopathologic Methods* and *Color Atlas of Special Stains and Tissue Artifacts*, 218–219 (1992). The Steiner technique, however, requires more steps, is more complex and takes considerably longer than the Warthin Starry process discussed above.

The methods of the invention are generally related to replacing the conventional gelatin solutions, used in existing stain protocols, with a solution of non-gelling gelatin, also referred to herein as partially hydrolyzed gelatin.

Non-gelling gelatin is hydrolyzed animal protein derived from collagen. It is produced, for example, from enzymatically modified gelatin. It has an approximate molecular weight of about 3,000 and an amino acid profile which is approximately the same as that of gelatin. Unlike gelatin, which is not soluble in cold water, i.e., water at room temperature, non-gelling gelatin is. The aqueous solutions of non-gelling gelatin of up to about 10% do not appreciably increase in viscosity. Above a concentration of about 10%, viscosity slowly increases. Solutions of about 50% concentration of non-gelling gelatin, for example, are quite viscous. Partially hydrolyzed gelatin is described in U.S. Pat. Nos. 4,147,772 and 4,338,335, both to McAleer et al., the teachings of which are incorporated herein by reference.

One specific example of non-gelling gelatin is currently available under the tradename Sol-U-Pro® and can be currently obtained from DynaGel, Inc., Calumet City, Ill. The characteristics of Sol-U-Pro® Type P, recommended for pharmaceutical applications, and Sol-U-Pro® type D, recommended for edible applications, are summarized in Tables 1–8.

TABLE 1

Sol-U-Pro ® P Properties

| | |
|---|---|
| Nitrogen Content | 15–17% |
| Viscosity | 4–6 cps (25% solution at 25° C.) |
| Bloom | 0 |
| Residue on Ignition | 3.0% Maximum |
| Loss on Drying | 2–6% |
| pH | 5.2–5.6 |
| Sulfate | 1.6% Maximum |
| Chloride | 1.0–2.5% |
| Heavy Metals | 50 PPM Maximum |
| Sulfur Dioxide | 40 PPM Maximum |

TABLE 2

Microbiological Specification of Sol-U-Pro ® P

| | |
|---|---|
| Total Aerobic Plate Count | 100/g Maximum |
| Thermophilic Plate Count | 100/g Maximum |
| Coliforms | Negative |
| E. coli | Negative |
| Salmonella sp. | Negative |
| Yeast & Molds | 10/g Maximum |

TABLE 3

General Nutritional Information of Sol-U-Pro ® P

| | |
|---|---|
| Protein | 88% to 92% |
| Fat | nil |
| Carbohydrates | nil |
| Moisture | 2.0% to 6.0% |
| Ash | 3.0% Maximum |
| Calories | 360 per 100 grams |
| Sodium | 500 PPM Maximum |
| Potassium | 200 PPM Maximum |
| Heavy Metals | 50 PPM Maximum |

TABLE 4

Typical Amino Acid Profile of Sol-U-Pro ® P

| | | | |
|---|---|---|---|
| Alanine | 8.6–10.7 | Leucine | 3.1–3.34 |
| Arginine | 8.3–9.1 | Lysine | 4.1–5.2 |
| Aspartic Acid | 6.2–6.7 | Methionine | 0.8–0.92 |
| Cysteine | Trace | Phenylalanine | 2.1–2.56 |
| Glutamic Acid | 11.3–11.7 | Proline | 16.2–18.0 |
| Glycine | 26.4–30.5 | Serine | 2.9–4.13 |
| Histidine | 0.85–1.0 | Threonine | 1.9–2.4 |
| Hydroxylysine | 0.09–1.18 | Tyrosine | 0.44–0.91 |
| Hydroxyproline | 13.0–14.1 | Valine | 2.5–2.8 |
| Isoleucine | 1.1–1.5 | | |

TABLE 5

Sol-U-Pro ® D Properties

| | |
|---|---|
| Average Molecular Weight | approximate 3,000 |
| Nitrogen Content | 16–17% |
| Viscosite | 4–6 cps (25% solution at 25° C.) |
| Bloom | 0 |
| Residue on Ignition | 10% Maximum |
| Loss on Drying | 4.0 to 8.5% |
| pH | 5.0 to 6.4 |
| Heavy Metals | 40 PPM Maximum |

TABLE 6

Microbiological Specification of Sol-U-Pro ® D

| | |
|---|---|
| Total Aerobic Plate Count | 500/g Maximum |
| Coliforms | Negative |
| E. coli | Negative |
| Salmonella sp. | Negative |

TABLE 7

General Nutritional Information of Sol-U-Pro ® D

| | |
|---|---|
| Protein | 90% to 95% |
| Fat | nil |
| Carbohydrates | nil |
| Moisture | 4.0% to 8.5% |
| Ash | 1.0% Maximum |
| Calories | 360 per 100 grams |
| Sodium | 500 PPM Maximum |
| Potassium | 100 PPM Maximum |
| Heavy Metals | 40 PPM Maximum |

TABLE 8

Typical Amino Acid Profile of Sol-U-Pro ® P

| Alanine | 8.6–10.7 | Leucine | 3.1–3.34 |
|---|---|---|---|
| Arginine | 8.3–9.1 | Lysine | 4.1–5.2 |
| Aspartic Acid | 6.2–6.7 | Methionine | 0.8–0.92 |
| Cysteine | Trace | Phenylalanine | 2.1–2.56 |
| Glutamic Acid | 11.3–11.7 | Proline | 16.2–18.0 |
| Glycine | 26.4–30.5 | Serine | 2.9–4.13 |
| Histidine | 0.85–1.0 | Threonine | 1.9–2.4 |
| Hydroxylysine | 0.09–1.18 | Tyrosine | 0.44–0.91 |
| Hydroxyproline | 13.0–14.1 | Valine | 2.5–2.8 |
| Isoleucine | 1.1–1.5 | | |

In a preferred embodiment of the invention, non-gelling gelatin, preferably in an aqueous solution, is dispensed at room, also referred to herein as ambient, temperature, from a liquid dispenser, in an automated histological staining method, such as described above. As used herein, room or ambient temperature refers to a temperature range from about 19° C. to about 25° C. In another preferred embodiment, non-gelling gelatin is used in an automated staining method based on the formation of silver metal by reacting a silver salt with a reducing agent. In a further preferred embodiment of the invention, non-gelling gelatin is used in an automated staining process employed in the detection of spirochetes.

For example, in a protocol based on the Warthin-Starry approach developed for an automated system such as the Artisan™ Staining System provided by CytoLogix™ Corporation, Cambridge, Mass., the gelatin solution is formed, for example, by combining 5 g of non gelling gelatin with 100 ml of deionized water. Optionally preservatives may be added as known in the art.

In alternative embodiments, gelatin solutions employed in existing staining protocols, including manual as well as automated processes, can be replaced with non-gelling gelatin solutions. For example aqueous solutions having lower viscosity for an equivalent gelatin content can be prepared by using non-gelling gelatin.

The invention is further described through the following examples which are provided for illustrative purposes and is not intended to be limiting.

EXAMPLES

Example 1

Protocol for the Steiner Method

A protocol for detecting the presence of microorganisms in a biological specimen in an automated system (Artisan™) which does not require gelatin and is based on the Steiner method is as follows. Common to all Artisan™ procedures is an initial aspiration of the Wash Solution (deionized water with a small amount of surfactant) that was placed on the slides during set-up.

1. Add 1 ml 1% uranyl nitrate solution to the slide, mix once, and heat to 62° C. for 600 seconds.
2. Remove the uranyl nitrate solution, rinse 3 times with 3 mL each time of Wash Solution.
3. Add 1 ml 1% silver nitrate solution to the slide, mix once, and heat to 60° C. for 600 seconds.
4. Remove the silver nitrate solution and rinse 3 times with 3 mL Wash Solution each time, then 2 rinses each of 3 mL 95% ethanol, then 1 rinse of 3 mL absolute ethanol.
5. Add 0.5 ml 2.5% gum mastic solution in alcohol to the slide, mix twice, and heat to 60° C. for 600 seconds.
6. Remove the gum mastic; add to the slide 0.5 mL ethanol, 1 mL gum mastic (2.5%) in ethanol, 1 mL 0.1% silver nitrate and 1 mL 4% hydroquinone and heat to 55° for 600 seconds. There are 2 mixes after adding gum mastic and after adding silver nitrate, and 6 mixes after adding hydroquinone.
7. Remove the mixture from step 6 and rinse 3 times with 3 mL each of Wash Solution, then twice with 3 mL each of 95% ethanol and finally with 3 mL of absolute ethanol.

The procedure requires 41 minutes to process one slide. A batch often slides can be run in 50 minutes. It has seven steps, after aspirating off the Wash Solution placed on the slide.

Example 2

Warthin Starry Protocol Using Non-Gelling Gelatin

In comparison with the procedure described in Example 1, The Warthin-Starry (W-S) procedure using non-gelling gelatin and developed for the Artisan™ system has basically four unique steps. For W-S, the initial aspiration of the Wash Solution is slightly different in that heating (to 60° C.) is started during this step. In other procedures, heating is only applied when reagents are added.

The unique steps are:

1. Add 1 mL non-gelling gelatin solution (5%) to the slide, maintain heating to 60° C. for 110 seconds.
2. Add 1 mL 1% silver nitrate solution to the slide, mix twice, maintain heating to 60° C. for 200 seconds.
3. Add 1 mL 0.13% hydroquinone solution to the slide, mix four times, maintain heating to 60° for 105 seconds.
4. Turn off the heat, aspirate the combined liquids from the slide, rinse once with 2 mL Wash Solution, twice with 3 mL each Wash Solution, once with 3 mL 95% ethanol, and twice with 3 mL each absolute alcohol.

With this procedure, the Artisan™ system takes 7 minutes 40 seconds to process one slide, and a batch of twelve is processed in about 30 minutes.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for staining a biological specimen comprising the steps of:
   (a) dispensing a solution including non-gelling gelatin onto the biological specimen;
   (b) dispensing a solution including a silver salt onto the biological specimen; and
   (c) dispensing a solution including a reducing agent onto the biological specimen;
   whereby the reducing agent reacts with the silver salt to produce silver metal, thereby staining the biological specimen.

2. The method of claim 1 wherein staining the biological specimen is in an automated histological staining process.

3. The method of claim 2 wherein the solution including non-gelling gelatin is dispensed from a liquid dispenser.

4. The method of claim 1 wherein the solution including non-gelling gelatin is an aqueous solution.

5. The method of claim 1 wherein the solution including non-gelling gelatin is dispensed at room temperature.

6. The method of claim 1 wherein the silver salt is silver nitrate.

7. The method of claim 1 wherein the reducing agent is hydroquinone.

8. The method of claim 1 wherein staining the biological specimen detects the presence of a microorganism.

9. The method of claim 8 wherein the microorganism is *Helicobacter Pylori*.

10. In a method for a histological staining of a biological specimen which includes reacting a silver salt with a reducing agent thereby forming silver metal, wherein the improvement comprises treating the biological specimen with a solution including non-gelling gelatin, a solution including a silver salt and a solution including a reducing agent.

11. In a method for detecting the presence of a microorganism in a biological specimen, said method including the selective deposition of silver metal, wherein the improvement comprises dispensing at room temperature, in an automated histological staining process, a non-gelling gelatin solution, a silver salt and a reducing agent onto the biological specimen.

12. In a method for detecting the presence of *Helicobacter pylori* in a biological specimen, said method including the selective deposition of silver metal, wherein the improvement comprises dispensing at room temperature, in an automated histological staining process, a non-gelling gelatin solution, a silver salt and a reducing agent onto the biological specimen.

13. A method for detecting the presence of a microorganism in a biological specimen in an automated histological staining process, comprising the steps of:

(a) treating the biological specimen with a solution including non-gelling gelatin;

(b) treating the biological specimen with a solution including a silver salt;

(c) treating the biological specimen with a solution including a reducing agent;

whereby the reducing agent reacts with the silver salt to produce silver metal and the silver metal stains the microorganism.

14. The method of claim 13 wherein the silver salt is silver nitrate.

15. The method of claim 13 wherein the reducing agent is hydroquinone.

16. The method of claim 13 wherein the microorganism is a spirochete or a bacterium.

17. The method of claim 16 wherein the spiral bacterium is *Helicobacter Pylori*.

18. The method of claim 13 wherein the solution including non-gelling gelatin is dispensed at room temperature.

19. The method of claim 13 wherein the solution including non-gelling gelatin is dispensed from a liquid dispenser.

20. The method of claim 13 wherein the solution including non-gelling gelatin is an aqueous solution.

21. A method for detecting the presence of *Helicobacter pylori* in a biological specimen in an automated histological staining process, comprising the steps of:

(a) treating the biological specimen with a solution including non-gelling gelatin;

(b) treating the biological specimen with a solution including a silver salt;

(c) treating the biological specimen with a solution including a reducing agent;

whereby the reducing agent reacts with the silver salt to produce silver metal and the silver metal stains *Helicobacter pylori*.

* * * * *